(12) United States Patent
O'Lenick

(10) Patent No.: US 8,680,304 B1
(45) Date of Patent: Mar. 25, 2014

(54) POLYGLYCEROL SILICONE POLYESTERS

(71) Applicant: Thomas George O'Lenick, Dacula, GA (US)

(72) Inventor: Thomas George O'Lenick, Dacula, GA (US)

(73) Assignee: Surfatech Corporation, Lawrenceville, GA (US)

( * ) Notice: Subject to any disclaimer, the term of this patent is extended or adjusted under 35 U.S.C. 154(b) by 0 days.

(21) Appl. No.: 13/986,024

(22) Filed: Mar. 25, 2013

Related U.S. Application Data

(60) Provisional application No. 61/689,894, filed on Jun. 15, 2012.

(51) Int. Cl.
  *C07F 7/02* (2006.01)
  *C07F 7/18* (2006.01)
(52) U.S. Cl.
  USPC ................................................ 554/77; 556/9
(58) Field of Classification Search
  USPC ................................................ 554/77; 556/9
  See application file for complete search history.

(56) References Cited

U.S. PATENT DOCUMENTS 7,638,116 B2   12/2009   LaVay

*Primary Examiner* — Deborah D Carr

(57) ABSTRACT

The present invention is directed toward a series of polyglycerol silicone polyesters with tunable ascetics and performance in cosmetic formulation. These novel polyglycerol silicone polyesters are designed to be high definition polymers. High Definition Polymers is meant that the polymer contains a variety of groups containing different chemical and physical properties that can be controlled by the polymerization process. High definition polymers are polymers are synthesized to have each portion of the polymer to achieve a desired aesthetics. These high definition polymers physical properties can be tuned quickly and easily but the polymerization conditions. The physical properties of the current invention can be tuned rapidly by controlling the ratio of fatty groups, as well as the cross-linker used. The resulting polyglycerol silicone polyesters have outstanding aesthetics, unique solubility and physical properties.

6 Claims, No Drawings

POLYGLYCEROL SILICONE POLYESTERS

RELATED APPLICATIONS

This application claims priority to and benefit of U.S. Provisional Application Nos. 61/689,849, filed Jun. 15, 2012, the disclosures of each of which are incorporated herein for all purposes.

FIELD OF THE INVENTION

The present invention is directed toward a series of polyglycerol silicone polyesters with tunable ascetics and performance in cosmetic formulation. These novel polyglycerol polyesters are designed to be High Definition Polymers. The physical properties of the current invention can be tuned rapidly by controlling the ratio of fatty groups, as well as the cross-linker used. Tuned here is meant the ability to adjust the physical properties to a desired value. The present invention allow for quick modification of cosmetic formulations, including but not limited to sunscreen formulations. The resulting polyglycerol silicone polyesters have outstanding aesthetics and physical properties.

BACKGROUND OF THE INVENTION

Polyglycerol compounds are well known materials. They are made by the condensation reaction of glycerin. The resulting products are polar and posses several un-related hydroxyl groups. The number of glycerin molecules condensed in the reaction is referred to as the degree of polymerization (DP).

Polyglycerol esters are also well known. They are the product of the esterfication reaction of polyglycerol and acids. Esterfication reactions run between an alcohol (polyglycerol) and a carboxylic acid produces water as a byproduct. U.S. Pat. No. 5,721,305 issued Feb. 24, 1998 to Eshuis, et al. entitled Polyglycerol production teaches how polydlycerol is made.

U.S. Pat. No. 3,936,391 issued Feb. 3, 1976 to Gabby entitled "Hydrated polyglycerol Ester Composition" teaches a polyglycerol ester emulsifier is prepared by heating a polyglycerol ester containing 3 to 10 glycerol units and a 1 to 2 saturated fatty acyl ester groups containing 16 to 20 carbon atoms, glycerol and water at a temperature of 125 to 135° F. The heat is maintained until a homogeneous paste-like consistency is imparted thereto.

U.S. Pat. No. 5,674,475 issued Oct. 7, 1997 to Dahms entitled "Emulsifier Composition based on Polyglycerol Ester" teaches an emulsifier composition of a mixture of polyglycerol fatty acid esters and the lactylate of a fatty acid or its salt. This emulsifier is used to manufacture a wide range of different oil in water emulsions.

U.S. Pat. No. 1,424,137 issued July 1922 to Weisberg, entitled "Polyglycerol Resins" discloses a polyglycerol ester of an aromatic dibasic acid used in shellac. This patent, imported herein by reference, addresses solid resins made in solvent. While lacking the critical control of cross-linking and producing a hard rather than a soft ester, this patent shows the state of the art in resins.

Still another U.S. Pat. No. 7,638,116, issued Dec. 29, 2009 by LaVay et al. entitled "Polyglycerol dimer polyester resins" discloses a polyglycerol dimer resin of a polyglycerol containing 3 to 10 repeat units cross-linked by dimer acid. While lacking the critical control of cross-linking and functionalization by fatty groups and silicone, this patent shows the state of the art of polyglycerol dimer polyesters.

A variety of patents exist that describe the use of dimethicone and dimethicone copoyol compounds used in cosmetic formulations, most notably is there use to foam alcohol sanitizers. They describe very generalized structures, most of which fail to function in other formulations.

Prior to the current invention, patents dealing with the use of dimethicone copolyol failed to recognize that there are significant structural differences between materials defined as dimethicone copolyols. Dimethicone and dimethicone copolyols exist in two major forms. These two major forms are named by the structure of the polymer backbone. The names are Comb and Terminal. The structures are:

Comb

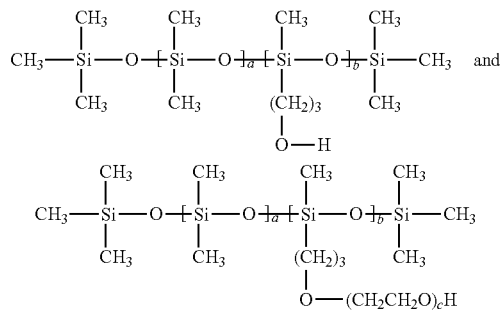

Terminal

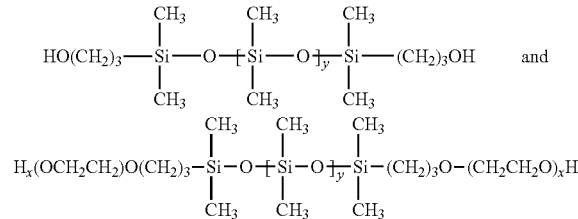

None of the references above understood the desirability of incorporation of fatty groups incorporated onto a polyglycerol backbone can modify the physical properties in cosmetic formulation. Furthermore, the incorporation of a silicone polymer crosslinker, either dimeticonol or dimethicone copolyol, will provide superior surface activity when compared to an organic crosslinker, provide unparalleled aesthesis, and unique solubility. These new high definition polymers produce a novel polymer that allows for the control of the solubility in alcohol, water, oil and silicone. Furthermore, the fatty groups allow for judicial control of physical, chemical and rheological properties of the polymer that will provide outstanding aesthesis when applied to hair, skin and fibers.

3

The Invention

Object of the Invention

The current invention is directed toward a series of high definition polyglycerol silicone polyesters that are synthesized by the reaction of polyglycerol, silicone succinate and a mixture of fatty acids. These high definition polyglycerol silicone polyesters contain a mixture of fatty groups with differing melt points. Since these polymers are high definition polymers the current invention will provide very unique physical properties and ascetics in cosmetic formulations.

SUMMARY OF THE INVENTION

The present invention is related to a series of novel polyglycerol silicone polyesters that are prepared by the reaction of a mixture of fatty acids, polyglycerol and a silicone succinate. The nature of a polymer that contains different physical properties mainly the difference between the water loving nature of polyglycerol, silicone loving portion of the crosslinker and the oil loving properties of the fatty groups provide the current invention unique properties. Furthermore, the physical properties of the fatty groups produce products that have extremely unique rheological and physical properties. The selection of the fatty groups, the silicone, and polyglycerol will drastically change the physical and cosmetic aesthetics of the resulting material.

The compounds of the present invention are made by the esterification reaction of a silicone succinate, polyglycerol, and a mixture of at least two fatty acids. The resulting products have the compatibility over those materials lacking the combination of these groups. This combination of groups results in a high efficient deposition of the skin, hair and fibers.

DETAILED DESCRIPTION OF THE INVENTION

The present invention is aimed at a series of novel high definition polyglycerol silicone polyester that provides desired ascetics and structure in cosmetic formulations.

Polyglycerol Silicone Polyester

A polyester having the following structure:

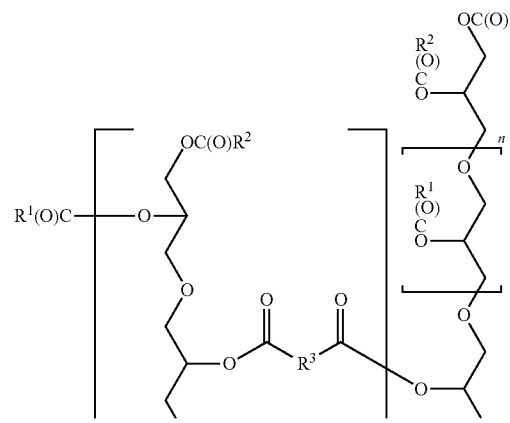

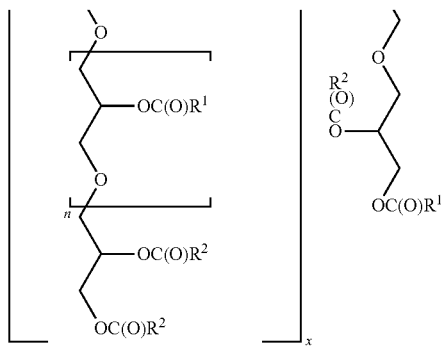

wherein;

$R^1$ is an alkyl containing 8 to 26 carbons, or mixtures thereof;

$R^2$ is an alkyl containing 8 to 26 carbons or mixtures thereof;

$R^3$ is independently selected from a dimethicone having the following structure:

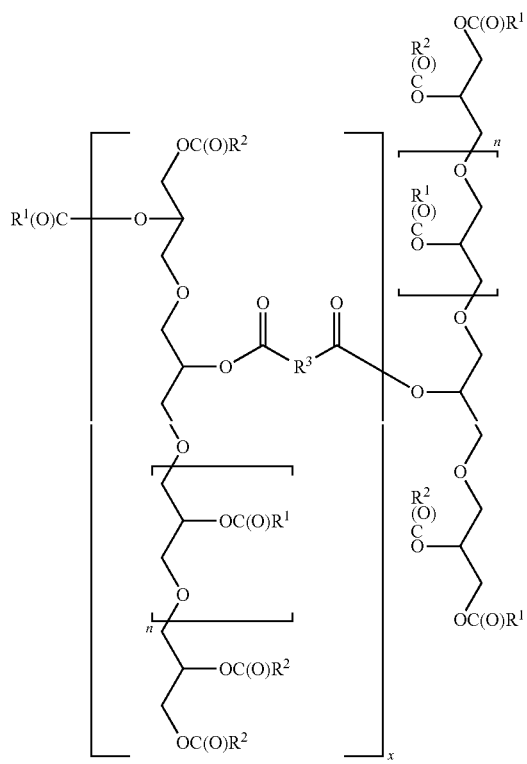

b is an integer ranging from 10 to 20;
or

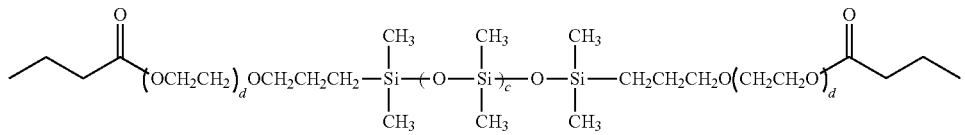

wherein;
c is an integer ranging from 10 to 20;
d is an integer ranging from 5 to 20;
or mixtures thereof;
n is an integer ranging from 0 to 9.

Preferred Embodiment

In a preferred embodiment $R^1$ and $R^2$ are different.

In a more preferred embodiment one of $R^1$ and $R^2$ is solid and the other is liquid. (as used herein, liquid is meant pourable at 25° C., by solid is meant solid at 25° C.).

In a more preferred embodiment $R^1$ is an alkyl having 18 carbons.

In a more preferred embodiment $R^3$ is linear dimethicone succinate where b is 10.

In a more preferred embodiment $R^2$ is an alkyl having 18 carbons.

In a more preferred embodiment $R^3$ is an alkyl having 7 carbons.

In a more preferred embodiment n is 0.

In a more preferred embodiment m is 0.

In a more preferred embodiment $R^3$ is Linear dimethicone copolyol succinate where b is 10 and a is 10.

Raw Materials

Fatty Acids

Fatty acids useful in the practice of the present invention are items of commerce commercially available from Cognis.

Fatty Acid Names

Fatty acids useful as raw materials in the preparation of compounds of the present invention are commercially available from a variety of sources including Procter and Gamble of Cincinnati Ohio. The structures are well known to those skilled in the art.

R—C(O)—OH

| | Saturated | | |
|---|---|---|---|
| Example | R Formula | Common Name | Molecular Weight |
| 1 | $C_7H_5$ | Caprylic | 144 |
| 2 | $C_9H_{19}$ | Capric | 172 |
| 3 | $C_{11}H_{23}$ | Lauric | 200 |
| 4 | $C_{13}H_{27}$ | Myristic | 228 |
| 5 | $C_{14}H_{29}$ | Pentadecanoic | 242 |
| 6 | $C_{15}H_{31}$ | Palmitic | 256 |
| 7 | $C_{17}H_{35}$ | Stearic | 284 |
| 8 | $C_{17}H_{35}$ | Isosteric | 284 |
| 9 | $C_{19}H_{39}$ | Arachidinic | 312 |
| 10 | $C_{21}H_{43}$ | Behenic | 340 |
| 12 | $C_{26}H_{53}$ | cetrotic | 396 |
| 13 | $C_{33}H_{67}$ | geddic acid | 508 |

| | Unsaturated | | |
|---|---|---|---|
| Example | R Formula | Common Name | Molecular Weight |
| 14 | $C_{17}H_{33}$ | Oleic | 282 |
| 15 | $C_{17}H_{31}$ | Linoleic | 280 |
| 16 | $C_{17}H_{29}$ | Linolenic | 278 |
| 17 | $C_{15}H_{29}$ | Palmitoleic | 254 |
| 18 | $C_{13}H_{25}$ | Myristicoleic | 226 |
| 19 | $C_{21}H_{41}$ | Erucic | 338 |

Polyglycerol

Polyglycerol is useful as raw materials in the preparation of compounds of the present invention. Polyglycerols are commercially available from a variety of sources including Solvay Chemicals of Rheinberg Germany.

The structures are well known to those skilled in the art.

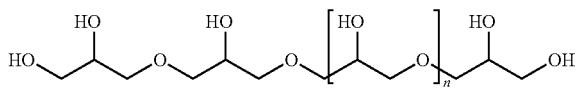

wherein;
n is an integer ranging from 0 to 9.

| Example | n | MW |
|---|---|---|
| 20 | 0 | 225.0 |
| 21 | 3 | 450.0 |
| 22 | 7 | 750.0 |

Linear Dimethicone Succinate

Linear Dimethicone Succinates are items of commerce available from Siltech LLC Lawrenceville, Ga. They conform to the following structure;

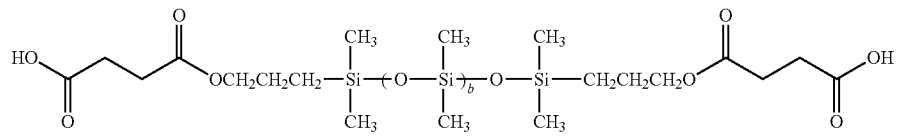

Wherein;
b is an integer ranging from 10 to 30;

| Example | B | Molecular Weight |
|---------|-----|------------------|
| 23 | 10 | 1,062.0 |
| 24 | 20 | 1,802.0 |
| 25 | 30 | 2,542.0 |

Linear Dimethicone Copoylols (LDMC)

LDMC are items of commerce available from Siltech LLC Lawrenceville, Ga. They have the following structure;

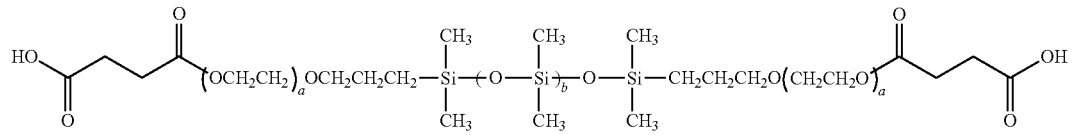

Wherein;
b is an integer ranging from 10 to 30;
a is an integer ranging from 5 to 20.

| Example | b | a | Molecular Weight |
|---------|-----|-----|------------------|
| 26 | 10 | 5 | 1,225.0 |
| 27 | 10 | 10 | 1,445.0 |
| 28 | 10 | 20 | 1,885.0 |
| 29 | 20 | 5 | 1,964.0 |
| 30 | 20 | 10 | 2,184.0 |
| 31 | 20 | 20 | 2,624.0 |
| 32 | 30 | 5 | 2,704.0 |
| 33 | 30 | 10 | 2,924.0 |
| 34 | 30 | 20 | 3,364.0 |

The values above were determined by $^{13}C$ NMR, $^{29}Si$ NMR and Gel Permeation Chromatography and do not rely upon any trade names.

General Procedure

A specified number of grams polyglycerol (examples 20-22) is added to a specified amount of fatty acids (examples 1-18) and silicone succinate (examples 23-34). The reaction mixture is heated to 160-180° C. Water is removed by vacuum during the reaction process. The reaction is monitored by the determination of acid value. The acid value will diminish as the reaction proceeds. The reaction is cooled once the acid value fails to change over an additional two hours at elevated temperature. The product is used without purification.

| | Polyglycerol | | $R^1$ | | $R^2$ | | $R^3$ | |
|---------|---------|-------|---------|-------|---------|-------|---------|-------|
| Example | Example | Grams | Example | Grams | Example | Grams | Example | Grams |
| 35 | 20 | 29.7 | 8 | 75.1 | 7 | 75.1 | 23 | 65.8 |
| 36 | 20 | 29.7 | 8 | 131.4 | 7 | 18.8 | 23 | 65.8 |
| 37 | 20 | 28.1 | 14 | 70.5 | 10 | 85.0 | 23 | 62.2 |
| 38 | 20 | 29.4 | 14 | 129.0 | 10 | 22.2 | 23 | 65.1 |
| 39 | 20 | 28.1 | 8 | 70.9 | 10 | 84.8 | 23 | 62.1 |
| 40 | 20 | 29.3 | 8 | 129.5 | 10 | 22.1 | 23 | 64.8 |
| 41 | 20 | 29.8 | 14 | 74.6 | 7 | 75.3 | 23 | 66.0 |

-continued

| | Polyglycerol | | $R^1$ | | $R^2$ | | $R^3$ | |
|---------|---------|-------|---------|-------|---------|-------|---------|-------|
| Example | Example | Grams | Example | Grams | Example | Grams | Example | Grams |
| 42 | 20 | 29.8 | 14 | 130.9 | 7 | 18.9 | 23 | 70.4 |
| 43 | 21 | 59.4 | 8 | 45.0 | 7 | 45.0 | 25 | 100.6 |
| 44 | 21 | 59.4 | 8 | 78.8 | 7 | 11.3 | 25 | 100.6 |
| 45 | 21 | 57.4 | 14 | 43.2 | 10 | 52.1 | 25 | 97.3 |
| 46 | 21 | 59.0 | 14 | 77.6 | 10 | 13.4 | 25 | 100.0 |
| 47 | 21 | 57.3 | 8 | 43.5 | 10 | 52.0 | 25 | 97.2 |
| 48 | 21 | 58.8 | 8 | 78.1 | 10 | 13.3 | 25 | 99.7 |
| 49 | 21 | 59.4 | 14 | 44.7 | 7 | 45.1 | 25 | 100.7 |
| 50 | 21 | 59.5 | 14 | 78.3 | 7 | 11.3 | 25 | 100.9 |
| 51 | 22 | 21.4 | 8 | 54.0 | 7 | 54.0 | 24 | 120.6 |
| 52 | 22 | 39.4 | 8 | 87.1 | 7 | 12.4 | 24 | 111.1 |
| 53 | 22 | 74.3 | 14 | 55.8 | 10 | 67.3 | 24 | 52.6 |
| 54 | 22 | 52.6 | 14 | 115.4 | 10 | 19.9 | 24 | 62.1 |
| 55 | 22 | 23.7 | 8 | 59.9 | 10 | 71.6 | 24 | 94.8 |
| 56 | 22 | 66.6 | 8 | 88.4 | 10 | 15.1 | 24 | 80.0 |
| 57 | 22 | 21.4 | 14 | 53.6 | 7 | 54.1 | 24 | 129.0 |
| 58 | 22 | 39.5 | 14 | 86.6 | 7 | 12.5 | 24 | 111.5 |
| 59 | 20 | 21.4 | 8 | 54.0 | 7 | 54.0 | 25 | 102.6 |
| 60 | 21 | 39.2 | 8 | 87.1 | 7 | 12.4 | 25 | 111.1 |
| 61 | 22 | 74.3 | 14 | 55.8 | 10 | 67.3 | 23 | 52.6 |
| 62 | 21 | 53.6 | 14 | 115.4 | 10 | 19.9 | 23 | 62.1 |
| 63 | 20 | 23.7 | 8 | 59.9 | 10 | 71.6 | 24 | 94.8 |
| 64 | 22 | 66.6 | 8 | 88.4 | 10 | 15.1 | 24 | 80.0 |
| 65 | 20 | 21.4 | 14 | 53.6 | 7 | 54.1 | 25 | 120.9 |
| 66 | 21 | 39.5 | 14 | 86.6 | 7 | 12.5 | 25 | 111.5 |
| 67 | 20 | 27.0 | 8 | 68.2 | 7 | 68.2 | 27 | 86.6 |
| 68 | 20 | 27.0 | 8 | 119.4 | 7 | 17.1 | 27 | 86.6 |
| 69 | 20 | 25.7 | 14 | 64.3 | 10 | 77.6 | 27 | 82.4 |
| 70 | 20 | 26.7 | 14 | 117.2 | 10 | 20.2 | 27 | 85.8 |
| 71 | 20 | 25.6 | 8 | 64.8 | 10 | 77.4 | 27 | 82.2 |
| 72 | 20 | 26.6 | 8 | 117.8 | 10 | 20.1 | 27 | 85.5 |
| 73 | 20 | 27.0 | 14 | 68.4 | 7 | 68.4 | 27 | 86.8 |
| 74 | 20 | 27.1 | 14 | 118.8 | 7 | 17.1 | 27 | 87.0 |
| 75 | 21 | 52.5 | 8 | 39.8 | 7 | 39.8 | 34 | 117.8 |
| 76 | 21 | 52.5 | 8 | 69.7 | 7 | 10.0 | 34 | 117.8 |
| 77 | 21 | 51.0 | 14 | 38.4 | 10 | 46.2 | 34 | 114.4 |
| 78 | 21 | 59.0 | 14 | 77.6 | 10 | 13.4 | 34 | 100.0 |

-continued

| Example | Polyglycerol Example | Grams | R¹ Example | Grams | R² Example | Grams | R³ Example | Grams |
|---|---|---|---|---|---|---|---|---|
| 79 | 21 | 50.9 | 8 | 38.6 | 10 | 46.2 | 34 | 114.2 |
| 80 | 21 | 52.1 | 8 | 69.2 | 10 | 11.8 | 34 | 116.9 |
| 81 | 21 | 52.6 | 14 | 39.6 | 7 | 39.9 | 34 | 118.0 |
| 82 | 21 | 52.7 | 14 | 69.3 | 7 | 10.0 | 34 | 118.1 |
| 83 | 22 | 43.8 | 8 | 55.4 | 7 | 55.4 | 29 | 95.5 |
| 84 | 22 | 43.8 | 8 | 96.9 | 7 | 13.8 | 29 | 95.5 |
| 85 | 22 | 42.0 | 14 | 52.7 | 10 | 63.5 | 29 | 91.7 |
| 86 | 22 | 43.5 | 14 | 95.3 | 10 | 16.4 | 29 | 94.8 |
| 87 | 22 | 42.0 | 8 | 53.1 | 10 | 63.4 | 29 | 91.6 |
| 88 | 22 | 43.3 | 8 | 95.8 | 10 | 16.4 | 29 | 94.5 |
| 89 | 22 | 43.9 | 14 | 55.0 | 7 | 55.5 | 29 | 95.7 |
| 90 | 22 | 43.9 | 14 | 96.3 | 7 | 13.9 | 29 | 95.9 |
| 91 | 20 | 18.5 | 8 | 46.7 | 7 | 46.7 | 34 | 138.1 |
| 92 | 21 | 34.4 | 8 | 76.1 | 7 | 10.9 | 34 | 128.6 |
| 93 | 22 | 69.0 | 14 | 51.6 | 10 | 62.6 | 27 | 66.5 |
| 94 | 21 | 48.3 | 14 | 105.9 | 10 | 18.2 | 27 | 77.5 |
| 95 | 20 | 22.9 | 8 | 57.9 | 10 | 69.2 | 29 | 100.0 |
| 96 | 22 | 64.7 | 8 | 85.9 | 10 | 14.7 | 29 | 84.7 |
| 97 | 20 | 18.5 | 14 | 46.4 | 7 | 46.8 | 34 | 138.3 |
| 98 | 21 | 34.5 | 14 | 75.7 | 7 | 10.9 | 34 | 128.9 |

Applications

The compounds of the present invention when added to alcoholic solutions, surprisingly and unexpectedly produce outstanding film formation and provide outstanding aesthetics to cosmetic formulations. Furthermore, the compounds of the present invention when added into a sunscreen formulation, surprisingly and unexpectedly produce water proofing and a dry skin feel.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein above but rather that the claims be construed as encompassing all the features of patentable novelty which reside in the present invention, including all features which would be treated as equivalents thereof by those skilled in the art to which the invention pertains.

The invention claimed is:

1. A polyglycerol dimethicone polyester prepared by the esterification reaction of:
    (a) fatty acid conforming to the following structure;

R—C(O)—OH wherein:
    R is an alkyl containing 8 to 26 carbons, or mixtures thereof;

(b) a polyglycerol having the following structure:

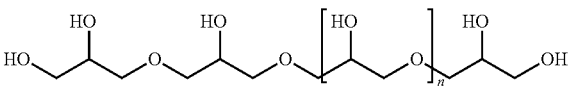

wherein;
    n is an integer ranging from 0 to 9;
    and
    (c) a dimethicone succinate selected from;

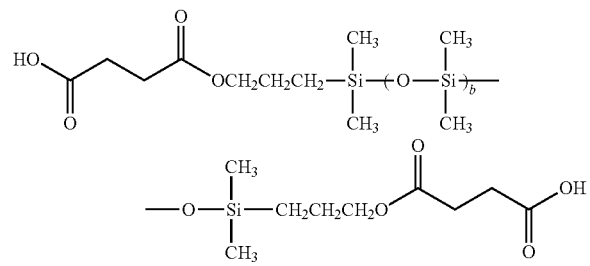

or

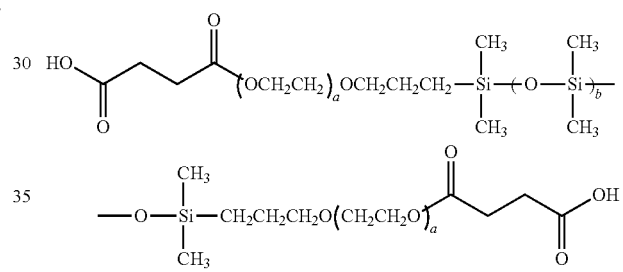

wherein;
    b is an integer ranging from 10 to 30;
    a is an integer ranging from 5 to 20.

2. A polyester of claim 1 wherein said esterification is carried out at a temperature of between 160 and 180° C.

3. A polyglycerol dimethicone polyester of claim 2 wherein b is 10.

4. A polyglycerol dimethicone polyester of claim 2 wherein b is 10.

5. A polyglycerol dimethicone polyester of claim 2 wherein R² is an alkyl having 18 carbons.

6. A polyglycerol dimethicone polyester of claim 2 wherein n is 0.

* * * * *